US012508401B2

(12) United States Patent
Piryk et al.

(10) Patent No.: US 12,508,401 B2
(45) Date of Patent: Dec. 30, 2025

(54) GUIDEWIRE PLACEMENT DEVICE

(71) Applicants: Christopher Piryk, Ocklawaha, FL (US); Alexis Bushman, Ocklawaha, FL (US)

(72) Inventors: Christopher Piryk, Ocklawaha, FL (US); Alexis Bushman, Ocklawaha, FL (US)

( * ) Notice: Subject to any disclaimer, the term of this patent is extended or adjusted under 35 U.S.C. 154(b) by 0 days.

(21) Appl. No.: 18/625,053

(22) Filed: Apr. 2, 2024

(65) Prior Publication Data

US 2025/0303116 A1 Oct. 2, 2025

(51) Int. Cl.
*A61M 25/02* (2006.01)

(52) U.S. Cl.
CPC ....... *A61M 25/02* (2013.01); *A61M 2025/028* (2013.01); *A61M 2205/0216* (2013.01); *A61M 2205/582* (2013.01); *A61M 2205/586* (2013.01); *A61M 2209/084* (2013.01); *A61M 2209/088* (2013.01)

(58) Field of Classification Search
CPC .................. A61M 25/02; A61M 25/09; A61M 2025/028; A61M 2025/0293; A61M 5/427; A61M 5/422; A61M 5/46
See application file for complete search history.

(56) References Cited

U.S. PATENT DOCUMENTS

| | | | | |
|---|---|---|---|---|
| 5,352,211 A * | 10/1994 | Merskelly | A61M 25/02 128/DIG. 26 |
| 2007/0225652 A1* | 9/2007 | Scherr | A61M 25/02 128/DIG. 26 |
| 2015/0164532 A1* | 6/2015 | Faller | A61B 17/320092 606/169 |
| 2019/0070391 A1* | 3/2019 | Dyall | A61M 25/01 |

* cited by examiner

*Primary Examiner* — Kevin C Sirmons
*Assistant Examiner* — Antarius S Daniel
(74) *Attorney, Agent, or Firm* — Tiffany C. Miller; Inventions International Inc.

(57) ABSTRACT

The present invention discloses a central venous catheter (CVC) extension device featuring a plate with a bore passing through it and an opening connecting to the bore, with two or more protrusion structures extending from the plate's second side. The opening's first end is linked to the bore, while its second end borders a section of the plate's outer perimeter edge. This device enhances the functionality and versatility of CVC extension devices, providing improved access and ease of use for medical professionals in various clinical settings.

19 Claims, 4 Drawing Sheets

GUIDEWIRE PLACEMENT DEVICE

BACKGROUND

The Seldinger technique finds broad application across various central venous cannulation procedures, encompassing tasks like radiographic medical imaging, chest drain or central venous catheter installation, percutaneous endoscopic gastrostomy tube insertion, and implantable medical device lead insertion, among others. Initially, a sharp hollow needle is employed to puncture and insert into a targeted blood vessel, cavity, or organ. Subsequently, a guidewire, featuring a rounded end, is threaded through the needle's lumen under continuous user control to prevent unintended displacement. After withdrawing the needle, it's substituted with tubing structures such as catheters, feeding tubes, or dilators, facilitating the introduction of medical instruments into the intended site. Following the insertion of the tubing, the guidewire is removed, and the tubing is secured, providing access for medication or resuscitation. Despite being a standard practice, inadvertent full-length guidewire insertion poses significant risks, often stemming from lapses during critical steps. Factors like operator inexperience, distraction, inadequate training, fatigue, or stress contribute to guidewire loss, leading to severe complications including embolism, arrhythmia, vascular damage, thrombosis, or even death. Detecting guidewire loss involves indicators like a missing guidewire, reduced backflow, or radiographic confirmation of its presence within the patient's body.

To address these challenges, there's a pressing need for guidewire retention and retraction devices integrated into central venous catheterization procedures. These devices ensure continuous guidewire control, mitigating the risk of its unintended advancement. Users, ranging from surgeons to healthcare professionals, benefit from these devices by eliminating the need for manual guidewire handling, thus enhancing procedural safety. Existing guidewire advancement devices lack the structural versatility required for retraction during central venous catheter placement, hindering their effectiveness. Therefore, there's a demand for removable guidewire retraction devices capable of accommodating obstructed guidewire ends, thus facilitating their easy removal post-procedure. Guidewire loss typically occurs post-needle insertion, especially during catheter advancement when manual guidewire control is absent. Additionally, to prevent oversight or omission, tubing structures with integrated or attachable guidewire retraction mechanisms are warranted. Despite the prior art, addressing these needs wasn't obvious to those skilled in the field, underscoring the novelty and significance of the present invention.

BRIEF DESCRIPTION OF THE DRAWINGS

The present disclosure may be better understood, and its numerous features and advantages made apparent to those skilled in the art by referencing the accompanying drawings. The use of the same reference symbols in different drawings indicates similar or identical items.

DETAILED DESCRIPTION

Figure 1:
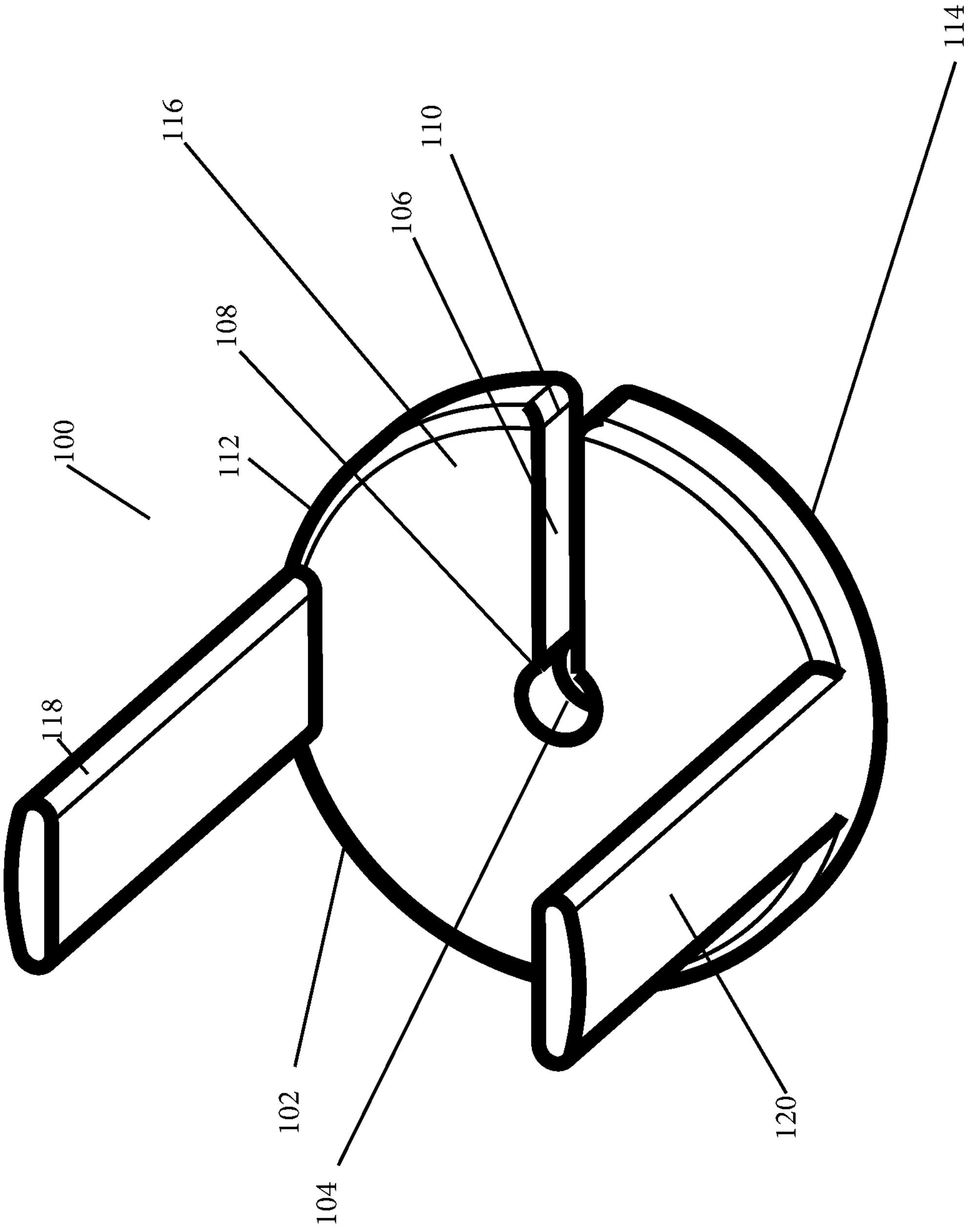
FIG. 1 is a diagram illustrating a rear perspective view of a CVC distancing apparatus in accordance with some embodiments.

FIGS. 1-6 illustrate a distancing apparatus with a double prong structure for employing a spacer guide removably connected to a central venous catheter (CVC). The CVC distancing apparatus presents an innovative structure to prevent guidewire loss during catheterization procedures. Featuring a plate with distinct first and second sides, it integrates a bore running through its thickness and an opening extending from the bore to the plate's outer perimeter. This opening facilitates the passage of the guidewire but does not directly create a viewing area. However, adjacent to the protrusion structures on the second side of the plate, there is a spacer that forms a dedicated viewing area. This area allows healthcare practitioners to observe the movement of the guidewire during the procedure, ensuring precise control. The bore is tailored to accommodate a portion of the CVC retaining the guidewire, securing its position, while the opening facilitates seamless guidewire passage. Importantly, the diameter of the bore exceeds the width of the opening, optimizing functionality. With the first side of the plate positioned proximal to the CVC and the second side facing the user receiving the guidewire, the apparatus ensures intuitive usability. The coplanar protrusion structures contribute to stability and ease of handling. Moreover, the plate's pliable material enables it to conform to the CVC's outer surface, ensuring a secure fit. In summary, this apparatus offers a comprehensive solution with a dedicated viewing area, empowering users to maintain precise control over the guidewire during catheterization procedures, thereby enhancing safety and procedural success.

The pliable material used in the CVC distancing apparatus serves a role in enhancing its functionality and compatibility during catheterization procedures. This material, which comprises the area bordering the bore on the plate, possesses flexibility and moldability, allowing it to deform and conform to the contours of the outer perimeter surface of the CVC. By adapting to the specific shape of the catheter, the pliable material ensures a snug and secure fit, minimizing the potential for movement or displacement during the procedure. This feature is particularly important for maintaining the stability of the guidewire and preventing its inadvertent loss or displacement. Additionally, the pliable nature of the material enhances user comfort and usability, as it provides a soft and accommodating surface for handling and manipulation. Overall, the incorporation of this pliable material in the CVC distancing apparatus contributes to its effectiveness in facilitating safe and successful catheterization procedures.

The material chosen for the plate of the central venous catheter (CVC) distancing apparatus is important for its functionality and usability during catheterization procedures. Typically, a pliable material is selected to ensure the plate can conform to the contours of the catheter and provide a secure fit. Silicone is often favored for its flexibility, biocompatibility, and resistance to deformation under stress. Its soft and malleable nature allows the plate to adapt to different shapes and sizes of catheters, ensuring a snug and secure fit without causing discomfort to the patient. Additionally, silicone's non-reactive properties make it suitable for medical applications, minimizing the risk of adverse reactions or complications. Polyurethane is another viable option known for its durability and elasticity, providing excellent support while maintaining flexibility. The pliable material used in the plate construction enhances the overall effectiveness and safety of the CVC distancing apparatus during central venous catheterization procedures.

FIG. 1 illustrates a distancing apparatus 100 including a plate 102 with a first side 116 located opposite a second side 114. The plate 102 has a bore 104 disposed through the plate 102. The plate 102 has an opening 106 which may be referred to as a slit or a slot traversing a portion of the plate 102. The opening 106 has a first end 108 connected to the bore 104 and a second end 110 bordering a portion of an outer perimeter edge 112 of the plate 102. Two or more protrusion structures such as first protrusion structure 118 and second protrusion structure 120 extend from the second side 114 of the plate 102.

In some aspects, the techniques described herein relate to a CVC extension device, wherein the bore of the plate is configured to receive a portion of the CVC (not shown) retaining a guidewire (not shown).

In some aspects, the techniques described herein relate to a CVC extension device, wherein the opening of the plate is configured to receive the guidewire.

In some aspects, the techniques described herein relate to a CVC extension device, wherein a diameter of the bore is greater in size than a width of the opening of the plate.

In some aspects, the techniques described herein relate to a CVC extension device, wherein the first side of the plate is configured to be proximal to the CVC and the second side of the plate is configured to be distal to the CVC and to be parallel to a user receiving a guidewire from the CVC.

In some aspects, the techniques described herein relate to a CVC extension device, further including: two protrusions of the two or more protrusions are substantially coplanar with the bore. The two or more protrusions are configured to abut and contact a portion of the patient receiving the guidewire from the procedure.

In some aspects, the techniques described herein relate to a CVC extension device, wherein the bore is located between each of the two protrusions of the two or more protrusions.

In some aspects, the techniques described herein relate to a CVC extension device, wherein the plate has a plurality of slits radiating from a perimeter edge of the bore, and wherein the plate having an area bordering the bore being is made of a pliable material configured to deform and conform to a portion an outer perimeter surface of the CVC.

In some aspects, the techniques described herein relate to a central venous catheter (CVC) distancing apparatus, including: a plate with a first side located opposite a second side including: a bore disposed through the plate; an opening having a first end connected to the bore and a second end bordering a portion of an outer perimeter edge of the plate; and two or more protrusion structures to extend from the second side of the plate.

In some aspects, the techniques described herein relate to a CVC distancing apparatus, wherein the bore of the plate is configured to receive a portion of the CVC retaining a guidewire.

In some aspects, the techniques described herein relate to a CVC distancing apparatus, wherein the opening of the plate is configured to receive the guidewire.

In some aspects, the techniques described herein relate to a CVC distancing apparatus, wherein a diameter of the bore is greater in size than a width of the opening of the plate.

In some aspects, the techniques described herein relate to a CVC distancing apparatus, wherein the first side of the plate is configured to be proximal to the CVC and the second side of the plate is configured to be distal to the CVC and to be oriented parallel to a user receiving a guidewire from the CVC.

The CVC distancing apparatus described herein represents an innovative solution designed to optimize the procedural workflow and enhance safety during central venous catheter (CVC) procedures. At its core, this apparatus features a specialized plate with distinct sides, each meticulously configured to serve specific functions within the procedural environment. The first side of the plate is strategically engineered to be in close proximity to the CVC insertion site. This positioning ensures optimal alignment with the catheter entry point, facilitating smooth and accurate placement of the guidewire. By being proximal to the CVC, this side of the plate plays a role in guiding the initial stages of the procedure, setting the foundation for subsequent steps with precision and confidence. Conversely, the second side of the plate is designed to be distal to the CVC, serving as a point of contact for the user or recipient or patient receiving the procedure. Positioned to be oriented parallel the user receiving the guidewire from the CVC, this side of the plate prioritizes ergonomic support and stability during guidewire manipulation. By offering a secure and comfortable interface for the user, it minimizes the risk of procedural errors or complications, ultimately enhancing the overall safety and efficiency of the procedure.

Together, these complementary sides of the plate form a cohesive apparatus that streamlines the CVC procedure, from initial insertion to guidewire manipulation. By effectively delineating the roles of each side in relation to the CVC and the user, this apparatus optimizes procedural outcomes while prioritizing patient safety and comfort.

In some aspects, the techniques described herein relate to a CVC distancing apparatus, further including: two protrusions of the two or more protrusions are substantially coplanar with the bore.

In some aspects, the techniques described herein relate to a CVC distancing apparatus, wherein the bore is located between each of the two protrusions of the two or more protrusions.

Within the structure of the CVC distancing apparatus, the second side of the plate incorporates two or more protrusion structures, strategically positioned to extend outward and interface with the user receiving a guidewire from the CVC. These protrusions serve as essential components of the apparatus, facilitating the guidance and manipulation of the guidewire during the procedure and providing a viewing window of the guidewire at the insertion site. The protrusion structures placement ensures direct contact with the user, enabling precise control and viewability throughout the procedure. By abutting the user receiving the guidewire, these protrusions enhance tactile feedback and proprioception, enabling a provider to navigate the guidewire with confidence and accuracy. Moreover, the structure of these protrusion structures prioritizes ergonomic considerations, ensuring comfort and ease of use for the user throughout the procedure. By incorporating these protrusion structures into the second side of the plate, the CVC distancing apparatus optimizes the user's visibility and interaction with the guidewire, promoting procedural efficiency and safety. Through their strategic placement and ergonomic structure, these structures enhance the overall user experience, contributing to successful outcomes in central venous catheter procedures.

In some aspects, the techniques described herein relate to a CVC distancing apparatus, wherein the plate has a plurality of slits radiating from a perimeter edge of the bore, and wherein the plate having an area bordering the bore being is made of a pliable material configured to deform and conform to a portion an outer perimeter surface of the CVC.

In some aspects, the techniques described herein relate to a spacer for a central venous catheter (CVC), including: a plate with a first side located opposite a second side including: a bore disposed through the plate; an opening having a first end connected to the bore and a second end bordering a portion of an outer perimeter edge of the plate; and two or more protrusion structures to extend from the second side of the plate.

In some aspects, the techniques described herein relate to a spacer, wherein the bore of the plate is configured to receive a portion of the CVC retaining a guidewire. The CVC is removably connected to the bore of the CVC distancing apparatus.

In some aspects, the techniques described herein relate to a spacer, wherein the opening of the plate is configured to receive the guidewire.

In some aspects, the techniques described herein relate to a spacer, wherein a diameter of the bore is greater in size than a width of the opening of the plate.

Figure 3:
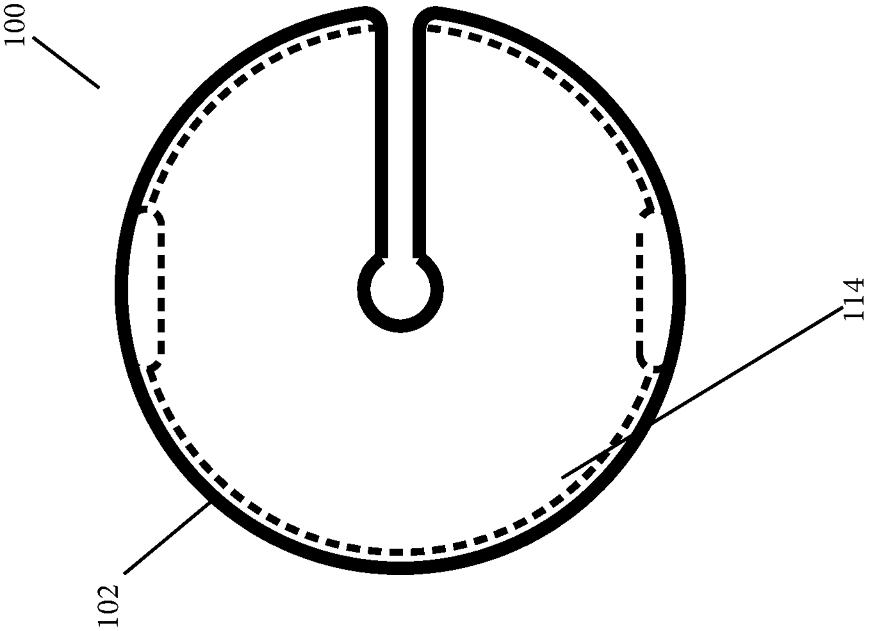
FIG. 3 is a diagram illustrating a top plan view of the CVC distancing apparatus of FIG. 1 in accordance with some embodiments.
Figure 2:
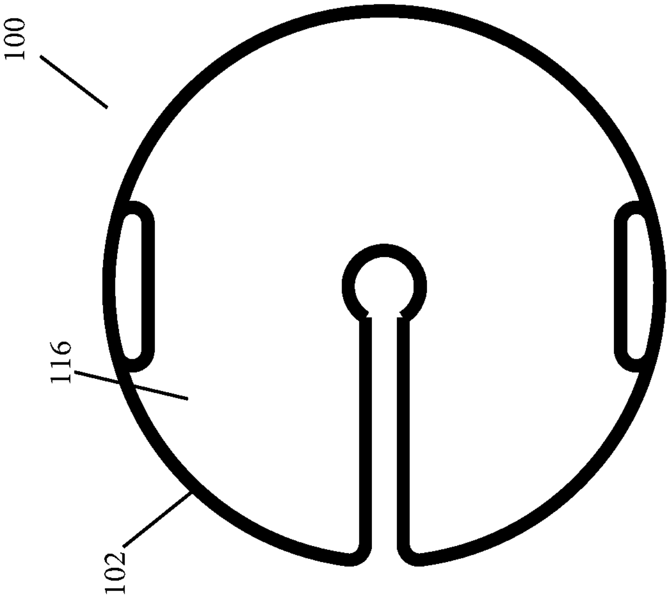
FIG. 2 is a diagram illustrating a rear plan view of the CVC distancing apparatus of FIG. 1 in accordance with some embodiments.

FIGS. 2 and 3 illustrate the distancing apparatus 100 of FIG. 1 including a plate 102 with the first side 116 (FIG. 2) located opposite the second side 114 (FIG. 3).

Figure 5:
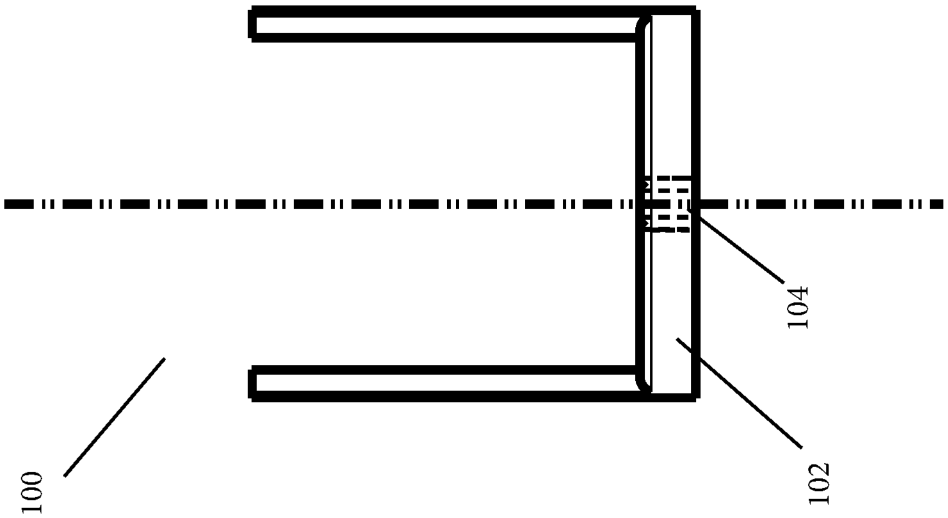
FIG. 5 is a diagram illustrating another side plan view of the CVC distancing apparatus of FIG. 1 in accordance with some embodiments.
Figure 4:
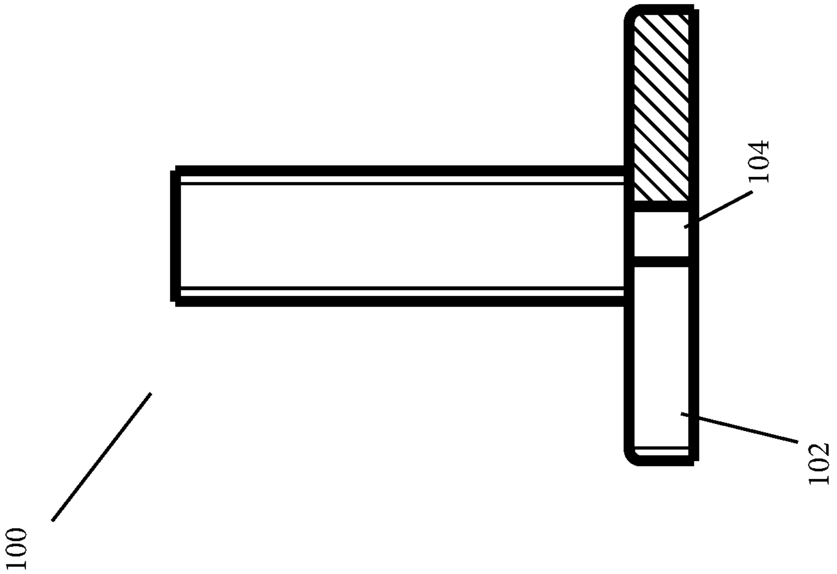
FIG. 4 is a diagram illustrating a side plan view of the CVC distancing apparatus of FIG. 1 in accordance with some embodiments.

FIGS. 4 and 5 illustrate the distancing apparatus 100 of FIG. 1 including the plate 102 having a bore 104 disposed through the plate 102.

Figure 6:
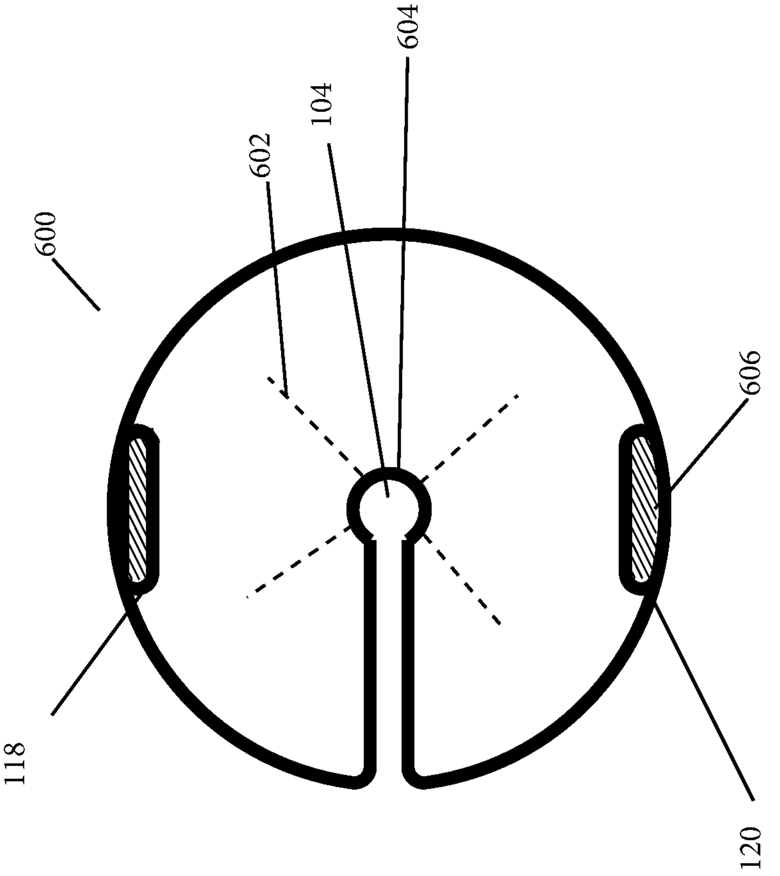
FIG. 6 is diagram illustrating a rear plan view of an embodiment of the CVC distancing apparatus of FIG. 1 with the plate having a plurality of slits radiating from a perimeter edge of the bore in accordance with some embodiments.

FIG. 6 is diagram illustrating an embodiment of the distancing apparatus 600 of FIG. 1 with the plate 102 having a plurality of slits 602 radiating from a perimeter edge 604 of the bore 104 in accordance with some embodiments. In FIG. 6, we observe an embodiment of the distancing apparatus 600, as depicted in FIG. 1, where the plate 102 features a distinctive configuration. The plate 102 is characterized by the presence of a plurality of slits 602 extending outward from the perimeter edge 604 of the bore 104. These slits 602 are arranged in a radial pattern, radiating outward like spokes from the central opening of the bore 104. The introduction of these slits 602 enhances the flexibility and adaptability of the distancing apparatus 600 during central venous catheter (CVC) procedures. By incorporating these slits 602 into the structure of the plate 102, the apparatus gains increased compliance and resilience, allowing it to conform more effectively to the contours of the CVC during insertion of the CVC into the bore of the plate. Furthermore, the arrangement of the slits 602 in a radial pattern ensures uniform distribution of flexibility across the plate 102, promoting balanced support and stability throughout the procedural workflow. This structural feature enhances the versatility of the distancing apparatus 600, accommodating variations in CVC sizes and procedural requirements with ease.

In some embodiments, the end of the two or more protrusion structures such as the first protrusion structure 118 and the second protrusion structure 120 may incorporate a gripping element 606, such as a plurality of ribs or gnarling, designed to prevent slippage and provide secure traction against the patient's skin. These ribs or gnarling features enhance the device's grip and stability, minimizing the risk of unintended movement or dislodgement during the procedure. By effectively anchoring the device in place, these gripping elements ensure precise positioning and promote procedural accuracy, ultimately enhancing patient safety and procedural success, a gnarling pattern can take various forms, including a criss-cross pattern or other configurations tailored to optimize grip and stability. The criss-cross pattern, characterized by intersecting lines or grooves, creates multiple points of contact with the skin, enhancing friction and resistance to movement. Alternatively, other patterns such as parallel lines, diagonal grooves, or textured surfaces may also be employed to achieve similar gripping effects. The choice of gnarling pattern depends on factors such as the device's intended application, material properties, and user preferences. Regardless of the specific pattern utilized, the primary objective remains consistent: to enhance traction and prevent slippage, thereby ensuring secure placement and reliable performance during medical procedures.

The plate 102 is crafted from a flexible material, such as medical-grade silicone or elastomer, known for its pliability and biocompatibility. This choice of material allows the plate 102 to seamlessly adapt to the shape and size of different CVCs. The flexibility of the material, combined with the presence of slits 602, ensures that the distancing apparatus 600 can be easily manipulated and positioned by healthcare practitioners, facilitating smooth and precise catheter placement. Overall, the presence of the slits 602 in the plate 102, coupled with the utilization of flexible materials, represents an innovative approach to optimizing the functionality and performance of the distancing apparatus 600 in central venous catheter procedures. Incorporating these slits not only enhances the device's flexibility but also reduces the necessity for multiple sizes of the extension device. By allowing the apparatus to adapt to different CVC sizes, the device becomes more versatile, potentially eliminating the need for healthcare providers to stock multiple sizes of extension devices. This simplifies inventory management, reduces costs, and streamlines procedural preparation, ultimately enhancing efficiency in clinical settings.

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific embodiments. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims. Moreover, the particular embodiments disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular embodiments disclosed above may be altered or modified and all such variations are considered within the scope of the disclosed subject matter. Accordingly, the protection sought herein is as set forth in the claims below.

What is claimed is:

1. A central venous catheter (CVC) extension device comprising:

a plate with a first side located opposite a second side comprising:

a bore disposed through the plate;

an opening having a first end connected to the bore and a second end bordering a portion of an outer perimeter edge of the plate; and two or more straight protrusion structures to extend from the first side of the plate, an entirety of each of the two or more straight protrusion structures are oriented perpendicular to the plate, the two or more straight protrusion structures are configured to abut and contact a portion of a user receiving a guidewire from a CVC, and wherein the two or more straight protrusion structures border a portion of the outer perimeter edge of the plate to form a viewing area located between the two or more straight protrusion structures.

2. The CVC extension device of claim 1, wherein the bore of the plate is configured to receive and retain a portion of the CVC and the CVC is configured to receive the guidewire.

3. The CVC extension device of claim 2, wherein the opening of the plate is configured to receive the guidewire.

4. The CVC extension device of claim 1, wherein a diameter of the bore is greater in size than a width of the opening of the plate.

5. The CVC extension device of claim 1, wherein the side of the plate is configured to be proximal relative to a user implementing the CVC over the guidewire and the first side of the plate is configured to be distal relative to the user implementing the CVC over the guidewire and the plate to be oriented substantially parallel to the user receiving the guidewire from the CVC.

6. The CVC extension device of claim 1, further comprising: two straight protrusion structures of the two or more straight protrusion structures are substantially coplanar with the bore.

7. The CVC extension device of claim 6, wherein the bore is located between each of the two straight protrusion structures of the two or more straight protrusion structures.

8. The CVC extension device of claim 1, wherein the plate has a plurality of slits radiating from a perimeter edge of the bore, and wherein the plate having an area bordering the bore being is made of a pliable material configured to deform and conform to a portion an outer perimeter surface of the CVC.

9. A central venous catheter (CVC) distancing apparatus, comprising:

a plate with a first side located opposite a second side comprising:

a bore disposed through the plate;

an opening having a first end connected to the bore and a second end bordering a portion of an outer perimeter edge of the plate; and two or more straight protrusion structures to extend from the first side of the plate, an entirety of each of the two or more straight protrusion structures are oriented perpendicular to the plate, the two or more straight protrusion structures are configured to abut and contact a portion of a user receiving a guidewire from a CVC, and wherein the two or more straight protrusion structures border a portion of the outer perimeter edge of the plate to form a viewing area located between the two or more straight protrusion structures, and wherein an end of the two or more straight protrusion structures have a gripping element, the gripping element is a plurality of ribs.

10. The CVC distancing apparatus of claim 9, wherein the bore of the plate is configured to receive and retain a portion of the CVC and the CVC is configured to receive the guidewire.

11. The CVC distancing apparatus of claim 10, wherein the opening of the plate is configured to receive the guidewire.

12. The CVC distancing apparatus of claim 9, wherein a diameter of the bore is greater in size than a width of the opening of the plate.

13. The CVC distancing apparatus of claim 9, wherein the second side of the plate is configured to be proximal relative to a user implementing the CVC over the guidewire and the first side of the plate is configured to be distal relative to the user implementing the CVC over the guidewire and the plate to be oriented substantially parallel to the user receiving the guidewire from the CVC.

14. The CVC distancing apparatus of claim 9, further comprising: two straight protrusion structures of the two or more straight protrusion structures are substantially coplanar with the bore.

15. The CVC distancing apparatus of claim 14, wherein the bore is located between each of the two straight protrusion structures of the two or more straight protrusion structures.

16. The CVC distancing apparatus of claim 9, wherein the plate has a plurality of slits radiating from a perimeter edge of the bore, and wherein the plate having an area bordering the bore being is made of a pliable material configured to deform and conform to a portion an outer perimeter surface of the CVC.

17. A spacer for a central venous catheter (CVC), comprising:

a plate with a first side located opposite a second side comprising:

a bore disposed through the plate;

an opening having a first end connected to the bore and a second end bordering a portion of an outer perimeter edge of the plate; and two or more straight protrusion structures to extend from the first side of the plate, an entirety of each of the two or more straight protrusion structures are oriented perpendicular to the plate, the two or more straight protrusion structures are configured to abut and contact a portion of a user receiving a guidewire from a CVC, and wherein the two or more straight protrusion structures border a portion of the outer perimeter edge of the plate to form a viewing area located between the two or more straight protrusion structures, and wherein an end of the two or more straight protrusion structures have a gripping element with a gnarling pattern, the gnarling pattern is a criss-cross pattern.

18. The spacer of claim 17, wherein the bore of the plate is configured to receive and retain a portion of the CVC and the CVC is configured to receive the guidewire.

19. The spacer of claim 18, wherein the opening of the plate is configured to receive the guidewire.

* * * * *